US009096631B2

(12) United States Patent
Stengel

(10) Patent No.: US 9,096,631 B2
(45) Date of Patent: Aug. 4, 2015

(54) EPIMERISATION OF SACCHARIDES

(75) Inventor: Bruno Frederic Stengel, Auderghem (BE)

(73) Assignee: CARGILL, INCORPORATED, Wayzata, MN (US)

( * ) Notice: Subject to any disclaimer, the term of this patent is extended or adjusted under 35 U.S.C. 154(b) by 184 days.

(21) Appl. No.: 13/578,520

(22) PCT Filed: Feb. 7, 2011

(86) PCT No.: PCT/EP2011/000550
§ 371 (c)(1),
(2), (4) Date: Aug. 10, 2012

(87) PCT Pub. No.: WO2011/098240
PCT Pub. Date: Aug. 18, 2011

(65) Prior Publication Data
US 2012/0309957 A1 Dec. 6, 2012

(30) Foreign Application Priority Data
Feb. 15, 2010 (EP) .................................... 10001498

(51) Int. Cl.
*C07H 3/02* (2006.01)
*C07H 3/04* (2006.01)
*C07H 1/00* (2006.01)
*B01J 19/00* (2006.01)

(52) U.S. Cl.
CPC ............... *C07H 3/02* (2013.01); *B01J 19/0093* (2013.01); *C07H 1/00* (2013.01); *B01J 2219/0086* (2013.01); *B01J 2219/00822* (2013.01); *B01J 2219/00826* (2013.01); *B01J 2219/00831* (2013.01); *B01J 2219/00833* (2013.01); *B01J 2219/00835* (2013.01); *B01J 2219/00869* (2013.01)

(58) Field of Classification Search
CPC ........ C07H 3/02; C07H 3/04; C08B 37/0006; B01J 19/0093
See application file for complete search history.

(56) References Cited

U.S. PATENT DOCUMENTS

| 4,029,878 | A | * | 6/1977 | Kruse ........................... 536/125 |
| 4,965,354 | A | * | 10/1990 | Yanaki et al. ................. 536/124 |
| 5,773,606 | A | * | 6/1998 | Vercauteren et al. ......... 536/124 |
| 6,437,190 | B1 | | 8/2002 | Leipprand et al. |
| 2007/0172931 | A1 | | 7/2007 | Harrison et al. |

FOREIGN PATENT DOCUMENTS

| EP | 0710501 | 5/1996 |
| EP | 1129772 | 9/2001 |
| EP | 1312411 | 5/2003 |
| WO | 95/17103 | 6/1995 |
| WO | 2009/021399 | 2/2009 |
| WO | W02011/098240 | 8/2011 |

OTHER PUBLICATIONS

Dellatre et al., J. Mol. Catal. B: Enzym., 2009, 60, p. 97-105.*
Fernandez et al., Avian Pathology, 2002, 31, p. 49-58.*
Ahmed-Omer et al., Org. Biomol. Chem., 2007, 5, p. 733-740.*
Kockritz at al., "Rearrangement of glucose to mannose catalysed by polymer-supported Mo catalysts in the liquid phase," Applied Catalysis A: General 334 (2008) 112-118.
PCT international Search Report of PCT/EP11/000550, mailed Nov. 8, 2011. 4 pages.

* cited by examiner

*Primary Examiner* — Jonathan S Lau

(57) ABSTRACT

The present invention relates to a process for an epimerization of a saccharide in a microdevice consisting of a network of micron-sized channels in presence of molybdenum containing catalyst. It further relates to the use of a microdevice consisting of a network of micron-sized channels for the epimerization reaction of saccharides and the oligomerization of the thus obtained epimerized saccharide, preferably into manno-oligosaccharides.

12 Claims, No Drawings

EPIMERISATION OF SACCHARIDES

CROSS-REFERENCE TO RELATED APPLICATIONS

This application claims benefit of international application PCT/EP2011/000550, filed Feb. 7, 2011, which application claims priority to European Application 10001498.4, filed Feb. 15, 2010, which applications are hereby incorporated by reference herein in their entirety.

FIELD OF THE INVENTION

The present invention relates to a process for epimerization and/or oligomerisation of saccharides, preferably for the preparation of mannose, and/or manno-oligomers, by using a microdevice consisting of a network of micron-sized channels.

BACKGROUND OF THE INVENTION

In order to continually improve physical standards of living for greater number of people, it is necessary to achieve more results with fewer resources. Therefore there is the tendency towards building and manufacturing smaller-scale products due to the desire for size efficiency. Most recently, scientists have learned that not only electronic devices, but also mechanical devices, may be miniaturized and batch-fabricated, promising the same benefits to the mechanical world as integrated circuit technology has given to the electronic world.

Saccharide epimerisation reactions are well known and it is in particular known that glucose may be epimerised to give an equilibrium mixture of glucose and mannose by means of a molybdenum catalyst. The earliest reference to this reaction is by V. Bilik in Chem. Zvesti, 26, 183-186 (1972) while U.S. Pat. No. 4,029,878, published 14 Jun. 1977, contains a description of a process using the catalytic reaction. Examples of suitable molybdenum catalysts given in U.S. Pat. No. 4,029,878 include molybdic acid, isopolymolybdic acids, heteropolymolybdic acids and acid salts such as sodium phosphomolybdate and silicomolybdic acid. This patent also describes the possibility of using as catalyst an anion exchange resin in which the hydroxyl ions have been replaced by molybdate ions.

A later Japanese patent JP 55076894 discloses the use of molybdate immobilised on anion exchange fibers. When activity of the molybdate-anion exchange fibre conjugate diminishes, the epimerisation process is stopped and the exhausted catalysator is leached off with alkali. Immobilisation of fresh molybdic acid on the original anion exchange fibre ensures a new active molybdate-anion exchange fiber conjugate.

European Patent 0 400 641 B1 also describes the use of molybdate exchanged anion exchange resin for epimerisation purposes. In this patent operation parameters are chosen in such a way that a minimal amount of bound molybdenum is leached out during epimerisation.

EP 0 710 501 describes the catalyst regeneration of a supported molybdenum catalyst.

Kockritz describes in Applied Catalysis A: General 334 (2008) pages 112-118, a rearrangement of glucose to mannose catalysed by polymer-supported molybdenum catalysts in the liquid phase.

Japanese patent publication (JP 4-368347, published 21 Dec. 1992) describes the use of a supported catalyst on a macroporous, strongly basic anion exchange resin.

In general, the benefits of miniaturized systems have been recognized but there is still a need for further developing the use of these systems in reactions for epimerization reactions and/or oligomerisation of saccharides.

SUMMARY OF THE INVENTION

The current invention relates to a process for the epimerisation of a saccharide wherein an aqueous solution containing the saccharide is fed into a microdevice consisting of a network of micron-sized channels and is contacted with a molybdenum-containing catalyst.

Furthermore the molybdenum-containing catalyst is provided in an aqueous solution or is supported on an inorganic or organic carrier.

The current invention relates to a process for preparing a mannose containing solution, the enrichment of the mannose and a oligomerisation of mannose-containing solutions into manno-oligosaccharides.

The current invention further relates to the use of a microdevice consisting of a network of micron-sized channels for epimerisation of saccharides.

The current invention further relates to a micron-sized channel of a microdevice consisting of a network of micron-sized channels and said channel is coated with molybdenum-containing catalyst.

Furthermore, the current invention relates to a molybdenum-containing catalyst supported on a carrier suitable for application in a microdevice consisting of a network of micron-sized channels.

Finally it relates to the use of the previously prepared manno-oligosaccharides into animal feed.

DETAILED DESCRIPTION

The current invention relates to a process for the epimerisation of a saccharide wherein an aqueous solution containing the saccharide is fed into a microdevice consisting of a network of micron-sized channels and is contacted with a molybdenum-containing catalyst. The contact is occurring in the microdevice consisting of a network of micron)sized channels. Preferably the microdevice is a micro reactor device consisting of a network of micron-sized channels etched into a solid substrate.

The saccharide, (=reactants or feedstocks) in the epimerisation reaction is containing at least one aldose or aldose analog. An aldose is a carbohydrate containing an aldehyde group. Those with 4 carbons are called tetroses those with 5 carbons are called pentoses, those with 6 are called hexoses, those with 7 heptoses and so forth. The tetroses consist of erythrose and threose. Included in the pentoses are ribose, arabinose, xylose and lyxose. The hexoses contain allose, altrose, glucose, mannose, gulose, idose, galactose and talose. Although the hexoses as a group, in particular glucose, may be the most important, the epimeric pentoses, ribose and arabinose are also important in the practice of the invention. A class of aldose analogs consists of n-deoxy-aldoses such as rhamnose, 6-deoxy-glucose, 4-deoxy-lyxose, 5-deoxy-arabinose, 4-deoxy-mannose and 5-deoxy-talose. Another class of aldose analogs includes aldose esters and ketals, such as glucose-6-acetate, mannose-5,6-dibutyrate, 4,6-O-ethylene-mannose and the like. Yet another class is that of uronic acids, such as alduronic acids, e.g. glucuronic acid, mannuronic acid, galacturonic acids and the like. Still other classes of aldose analogs are that of the 6-deoxy-6-amino-aldoses, the 4,5 or 6-O-alkyl aldoses and the 4-, 5- or 6-deoxy haloaldoses. Preferably the saccharide is glucose.

The concentration of the saccharide is not important in the practice of the invention, although as a practical consideration it is advantageous to have the solutions as concentrated as possible consistent with viscosity requirements. The saccharide solution fed into the microdevice consisting of a network of micron-sized channels, comprises 10 to 90% by weight dry substance, preferably 15% to 80% by weight, more preferably 40% to 70% by weight dry substance most preferably 50% to 60%. The saccharide solution can be applied at 35%, 45% and 55%, 65% and 75% dry substance as well.

The pH at which the epimerisation reaction is effected can have an influence on the activity and stability of the molybdenum-containing catalyst and is in the range of 0.1 to about 8.0, in the range of 0.5 to 7, preferably in the range of 0.5 to 6, in the range of 1 to 4, more preferably in the range of 1 to 3.

The epimerisation reaction is usually performed in a temperature range between about 40° C. and 250° C., preferably from 60 to 180° C., more preferably from 70 to 150° C. Effective epimerisation can also be obtained at temperatures of 100 to 120° C.

The time over which the epimerisation is conducted will be quite variable depending upon the reaction temperature, the catalyst amount, the extent of conversion sought and the microdevice consisting of a network of micron-sized channels. Consequently the epimerisation will run for a time sufficient to achieve a commercial acceptable product distribution. Preferably the reaction time is less than 30 minutes, less than 15 minutes, less than 10 minutes, more preferably less than 5 minutes, about 5 minutes, about 2.5 minutes, and even most preferably less than 1 minute.

Microdevices consisting of a network of micron-sized channels (also known as microreactors) are usually defined as miniaturized reaction vessels fabricated at least partially, by methods of microtechnology and precision engineering. The characteristics dimensions of the internal structure of microreactor fluid channels (micron-sized channels) can vary substantially, but typically range from the sub-micrometer to the sub-millimeter range. Microreactors most often are designed with microchannel architecture. These structures contain a large number of channels and each micron-sized channel is used to convert a small amount of material. A number of materials such as silicon, quartz, glass, metals and polymers have been used to construct micro reactors. Depending on the material used, a range of channel micro fabrication methods such as photolithography, hot embossing, powder blasting, injection moulding and laser micro forming are available. P.D.I Fletcher provides in Tetrahedron report 609 (Tetr. 58 (2002), 4735-4757) a review of microreactors, the principles and applications in organic synthesis.

The benefits of miniaturized systems, designed with dimensions similar to microreactors (microdevices), compared to a large scale process include but are not limited to the following advantages, large scale batch process can be replaced by a continuous flow process, smaller devices need less space, fewer materials, less energy and often shorter response times and system performance is enhanced by decreasing the component size, which allows integration of a multitude of small functional elements. Consequently, microreactors (microdevices) significantly intensify heat transfer, mass transport, and diffusional flux per unit volume or unit area. The current invention benefits from increased reaction speed, high conversion rate and/or reduced diminution of the catalyst activity (=low leaching) by applying a microdevice consisting of a network of micron-sized channels.

Typical thickness of the fluid layer in a microreactor can be set to few tens of micrometers (typically from about 10 µm to about 1 mm) in which diffusion plays a major role in the mass/heat transfer process. Preferred typical dimensions are in the range of 10 to 300 µm. Due to a short diffusional distance, the time for a reactant molecule to diffuse through the interface to react with other molecular species is reduced to milliseconds and in some cases to nanoseconds. Therefore the conversion rate is significantly enhanced and the chemical reaction process appears to be more efficient.

The epimerisation reaction is effected by any molybdenum-containing catalyst of Mo(VI) whose solubility in aqueous solution is at least 100 ppm at some point within the pH range of 0.1 to 8.0. Examples of suitable molybdenum catalysts are given in U.S. Pat. No. 4,029,878 and include molybdic acid, isopolymolybdic acids, heteropolymolybdic acids and acid salts such as sodium phosphomolybdate and silicomolybdic acid. Molybdate salts, i.e. salts of $MoO_4$ dianion are most commonly used in epimerisation reactions of saccharides and they include molybdate salts of sodium, potassium, lithium, calcium, strontium, zinc, iron(II), magnesium, ammonium and barium and the like. Organo-metallic molybdate complexes such as molybdenum(VI) oxide bis(2,4-pentanedionate), also may be used in the practice of this invention as well as molybdenum trioxide which usually is considered a water-insoluble material but whose solubility is sufficient to satisfy the criteria articulated above. The epimerisation can in fact be affected by any molybdenum species in solution or supported on an inorganic or organic carrier where it is placed on an exchangeable site convertible to a molybdenum (VI) oxy anion.

A typical example of a suitable organic carrier is an anion exchange resin, and especially a strong anion exchange resin which has been exchanged with molybdate over a particular pH range. The anion exchange resin may be of the gel or macroreticular type, with its particular nature not being of special significance.

The supported catalyst may be prepared by contacting the support with an aqueous solution of the molybdenum compound suitably at ambient temperature for a period of time sufficient to achieve the desired loading of the catalyst on the support eg. up to 12 hours. The pH of the solution of the molybdenum compound in contact with the support is advantageously in the range 0.5 to 7, preferably 1.0 to 5.5. The preferred loading of the molybdenum compound catalyst on the support will vary from support to support but may be determined by simple experiment. Too high a loading for a given support should be avoided because of the disadvantage of an increased leaching of molybdenum from the support into the solution during the epimerisation reaction.

The supported organic carrier can be applied in the microreactor such that a heterogeneous mixture is provided into the microreactor. The size of the resin beads will be adapted to the size of the micron-sized channels of the microdevice consisting of a network of micron-sized channels. Alternatively at least one micron-sized channel is supported with, coated with, or equipped with the molybdenum-containing catalyst.

The inorganic carrier is selected such that the molybdenum catalyst is incorporated into, supported on, coated on, attached to the carrier in order to allow a smooth epimerisation reaction and yet a low leaching of the molybdenum is occurring during the epimerisation reaction. Furthermore, the inorganic carrier allows a type of attachment to at least one micron-sized channel of the microdevice consisting of a network of micron-sized channels. Preferably more than one, more preferably several or all micron-sized channels of the microdevice consisting of a network of micron-sized channels are supported with, coated with, or equipped with the molybdenum-containing catalyst.

The current invention further relates to a molybdenum-containing catalyst supported on a carrier suitable for application in microdevice consisting of a network of micron-sized channels.

The process of the current invention can run in batch, semi-continuously, pulse or continuously, preferably continuously. The selectivity of the epimerisation reaction can be further increased by adding other components such as boron compounds, being provided in aqueous solution or supported on a carrier, which in turn can be attached to, incorporated into, supported on (=micron-channel is coated with) at least one micron-sized-channel of the microdevice consisting of a network of micron-sized channels.

Furthermore, the selectivity of the epimerisation reaction can be affected by supplying the saccharide in an aqueous solution or a non-aqueous solution, such as alcohols and/or ethers. Suitable alcohols and ethers are methanol, ethanol, glycerol, ethylene glycol or ethylene glycol ether and mixtures thereof, either alone or in combination with water.

In a preferred embodiment, the process of the current invention comprises the use of glucose solutions as the saccharide. The aqueous solution of the glucose is passed through a microdevice consisting of a network of micron-sized channels and which is containing a molybdenum-containing catalyst. The epimerisation can be homogeneously catalysed (i.e. the molybdenum-containing catalyst is provided in solution), preferably heterogeneously catalysed whereby the molybdenum-containing catalyst is attached to, incorporated into supported on (=micron-channel is coated with) at least one micron-sized-channel of a microdevice or whereby the molybdenum-containing catalyst is provided on a carrier that in turn can be attached to, incorporated into at least one micron-sized-channel of a microdevice consisting of a network of micron-sized channels.

Upon finalising the epimerisation reaction in the microdevice consisting of a network of micron-sized channels, the obtained mannose containing solution is collected.

Although not required by the current invention, the mannose containing solution may optionally be subjected to conventional ion exchange chromatography.

The reaction (=epimerized saccharide) solution (is mannose containing solution) or optionally the solution obtained after the ion exchange treatment is then subjected to liquid chromatography so as to provide at least one fraction which is enriched in mannose content. Optionally mannose is isolated from this enriched mannose solution.

Furthermore, the current invention further relates to a process wherein the mannose containing solution, the enriched mannose containing solution, the isolated mannose or mixture of two or more thereof are oligomerised to a manno-oligosaccharide containing composition by applying a microdevice consisting of a network of micron-sized channels and in presence of an acidifying catalyst.

These acidifying catalysts comprise one or more mineral acids such as hydrochloric acid, sulphuric acid, sulphurous acid, thiosulfuric acid, dithionic acid, pyrosulfuric acid, selenic acid, selenious acid, phosphorous acid, boric acid, perchloric acid, hypochlorous acid, hypobromic acid, hydroiodic acid, silicic acid, acidic alkali metal or alkaline earth metal salts of the above acids such as sodium bisulphate and sodium bisulfite, or mixture of these acids (and/or acidic alkali or alkaline earth metals salts) with phospohoric acids, or acids which are allowable for consumption in order to reduce the otherwise necessary controls and costs to check for the presence of and, if necessary, remove the catalyst acids from the final product. In particular, the edible acids (food grade acids) are phosphoric acid, citric acid, malic acid, succinic acid, adipic acid, gluconic acid, tartaric acid, fumaric acid and mixtures thereof. Particularly preferred are citric acid and/or phosphoric acid. The amount of acid to be used as catalyst should be below 15 weight % relative to the amount of saccharide starting material used in the oligomerisation reaction. Preferably, this amount should be clearly below this level, such as e.g. at most 12 weight %, at most 10 weight %. The addition of the acid can be done in any vessel but might occur in the microdevice consisting of a network of micron-sized channels as well. Before injecting the carbohydrate containing mixture through the microdevice consisting of a network of micron-sized channels, the mixture can be heated by using a micro-heat-exchanger and/or microwaves or any other suitable heating device.

The temperature of the oligomerisation is from 100° C. to 350° C., preferably from 150° C. to 250° C., more preferably from 180° C. to 200° C.

Before collecting the oligomers, the product can be cooled by using a micro heat exchanger.

In oligomerisation reactions, one is usually interested in obtaining a product of specific molecular weight or a range of products with specific molecular weights, since the properties of the oligomers will usually be dependent on molecular weight. Molecular weights higher or lower than the desired weights are equally undesirable. Since the degree of oligomerisation is a function of reaction time, the desired molecular weight can be obtained by quenching the reaction at the appropriate time. It has been seen that by applying a microdevice consisting of a network of micron-sized channels, the reaction time which usually takes at least 1 to 2 hours, even up to 6 hours, can be reduced to less than 30 minutes, preferably less than 15 minutes, preferably less than 10 minutes, preferably less than 5 minutes.

Manno-oligosaccharides prepared according to the process of the current invention are oligosaccharides having a repeating saccharide entity (predominantly mannose) of at least 2 and up to 20. The manno-oligosaccharides may further comprise alpha and beta linkages, linear and/or branched, as well as 1,2-, 1,3-, 1,4- and 1,6-linkages and mixtures thereof.

The current invention further relates to the use of a microdevice consisting of a network of micron-sized channels for epimerisation reactions of saccharides, preferably for the epimerisation of glucose into mannose.

Furthermore, the current invention relates to a (at least one) micron-sized-channel of a microdevice consisting of a network of micron-sized channels and said micron-sized channel is supported with, coated with, incorporated with, or equipped with molybdenum containing catalyst. Consequently, a microdevice consisting of a network of micron-sized channels wherein at least one micron-sized-channel is supported with, coated with, incorporated with or equipped with molybdenum containing catalyst is part of this current invention as well. Preferably more than one, more preferably several micron-sized channels, most preferably most or all of the micron-sized channels of the microdevice consisting of a network of micron-sized channels are supported with, coated with, incorporated with, or equipped with molybdenum-containing catalyst in order to further improve the efficiency and selectivity of the epimerisation reaction.

The current invention further relates to the use of the previously prepared manno-oligosaccharides in animal feed. These newly prepared manno-oligosaccharides can act as inhibitors of pathogen adhesion to mammalian cells, especially mammalian gut cells. These manno-oligosaccharides may be provided as part of a meal and may be nutritionally completed with vitamins, minerals, trace elements as well as nitrogen, carbohydrate and fatty acid sources.

The invention will hereunder be illustrated in the form of the following examples.

EXAMPLES

Example 1

Crystalline Dextrose monohydrate (Cargill C*Dex 02001) was solubilised in water to prepare a glucose solution at 50% solids content. Ammonium heptamolybdate (Merck, Art. 1182, Lot no.: 2522795) was added in an amount of 0.2 g per 100 g glucose dry substance. The resulting solution was pumped at a rate of 0.5 ml/min to a micro heat exchanger (Kreuzstromreaktormodul 1694-X-19.0, KIT, IMVT) which increased the product temperature to 150° C. The residence time in the micro reactor was 5 minutes. The reaction solution mass was then conveyed continuously into a second micro heat exchanger (Kreuzströmer 678-K-1.3, KIT, IMVT) where the product was cooled down to ambient temperature. The solution left the micro heat exchanger via a pressure holding valve which kept the pressure in the micro reactor system at ca. 4.8 bar. The HPLC analysis (ISO 10504:1998-10, using a Pb-column (Biorad HPX87P) instead of the mentioned Ca-column) showed a Mannose content of the final solution of 30% based on the total carbohydrate content.

Example 2

Crystalline Dextrose monohydrate (Cargill C*Dex 02001) was solubilised in water to prepare a glucose solution at 50% solids content. Ammonium heptamolybdate (Merck, Art. 1182, Lot no.: 2522795) was added in an amount of 0.2 g per 100 g glucose dry substance. The resulting solution was pumped at a rate of 1 ml/min to a micro heat exchanger (Kreuzstromreaktormodul 1694-X-19.0, KIT, IMVT) which increased the product temperature to 150° C. The residence time in the micro reactor was 2.5 minutes. The reaction solution mass was then conveyed continuously into a second micro heat exchanger (Kreuzströmer 678-K-1.3, KIT, IMVT) where the product was cooled down to ambient temperature. The solution left the micro heat exchanger via a pressure holding valve which kept the pressure in the micro reactor system at ca. 4.8 bar. The HPLC analysis (ISO 10504:1998-10, using a Pb-column (Biorad HPX87P) instead of the mentioned Ca-column) showed a Mannose content of the final solution of 26% based on the total carbohydrate content.

The invention claimed is:

1. A process for the epimerisation of a saccharide, the process comprising: a) providing a molybdenum-containing catalyst that is fixed onto an inorganic carrier; b) applying the molybdenum-containing catalyst into a microdevice, wherein the microdevice consists of a network of micron-sized channels and the molybdenum-containing catalyst is attached to, incorporated into, or supported on at least one micron-sized channel of the microdevice; and c) feeding an aqueous solution containing the saccharide into the microdevice, thereby contacting the aqueous solution with a molybdenum-containing catalyst to provide an epimerized saccharide.

2. The process of claim 1, wherein the epimerisation reaction is run for less than about 5 minutes.

3. The process of claim 1, wherein the epimerisation reaction is run for less than about 2.5 minutes.

4. The process of claim 1, wherein the epimerisation reaction is run for less than about 1 minute.

5. The process of claim 1, wherein the saccharide is glucose and the epimerized saccharide is mannose.

6. The process of claim 5, further comprising: d) oligomerizing the epimerized saccharide in a microdevice consisting of a network of micron-sized channels to provide manno-oligosaccharides.

7. The process of claim 5, further comprising: d) oligomerizing the epimerized saccharide in a microdevice consisting of a network of micron-sized channels in the presence of an acidifying catalyst to provide manno-oligosaccharides.

8. The process of claim 5, further comprising: e) feeding the epimerized saccharide-containing solution into a microdevice consisting of a network of micron-sized channels and in the presence of an acidifying catalyst to allow for oligomerisation of the epimerized saccharide-containing solution into manno-oligosaccharides.

9. The process of claim 5, further comprising: d) enriching mannose of the epimerized saccharide-containing solution to provide an enriched-mannose solution.

10. The process of claim 9, further comprising: e) feeding the enriched mannose solution or a mixture of the enriched mannose solution with the epimerized saccharide-containing solution into a microdevice consisting of a network of micron-sized channels and in the presence of an acidifying catalyst to allow for oligomerisation of the enriched mannose solution or a mixture of the enriched mannose solution with the epimerized saccharide-containing solution into manno-oligosaccharides.

11. The process of claim 9, further comprising: f) isolating mannose from the enriched-mannose solution.

12. The process of claim 11, further comprising: g) feeding the mannose-containing solution, the enriched mannose solution, the isolated mannose, or a mixture of two or more thereof into a microdevice consisting of a network of micron-sized channels and in the presence of an acidifying catalyst to allow for oligomerisation of the mannose-containing solution, the enriched mannose solution, the isolated mannose, or a mixture of two or more thereof into manno-oligosaccharides.

* * * * *